(12) United States Patent
Sakai et al.

(10) Patent No.: US 8,017,046 B2
(45) Date of Patent: Sep. 13, 2011

(54) SKIN COSMETIC COMPOSITION

(75) Inventors: Shigefumi Sakai, Sumida-ku (JP);
Atsuyuki Kiba, Sumida-ku (JP);
Chitoshi Shigeno, Wakayama (JP);
Hideaki Kubo, Wakayama (JP)

(73) Assignee: Kao Corporation, Tokyo (JP)

( * ) Notice: Subject to any disclaimer, the term of this patent is extended or adjusted under 35 U.S.C. 154(b) by 190 days.

(21) Appl. No.: 12/390,390

(22) Filed: Feb. 20, 2009

(65) Prior Publication Data

US 2009/0155323 A1 Jun. 18, 2009

Related U.S. Application Data

(62) Division of application No. 09/892,577, filed on Jun. 28, 2001, now abandoned.

(30) Foreign Application Priority Data

| Jun. 30, 2000 | (JP) | 2000-198543 |
| Jun. 30, 2000 | (JP) | 2000-199401 |
| Aug. 14, 2000 | (JP) | 2000-245708 |
| Aug. 14, 2000 | (JP) | 2000-245709 |

(51) Int. Cl.
*B01J 13/02* (2006.01)
*B01J 13/04* (2006.01)
*A61K 8/11* (2006.01)

(52) U.S. Cl. ............... 264/4.1; 264/4.3; 264/4.4; 264/9; 424/401

(58) Field of Classification Search ............... 264/9, 4.1, 264/4.3, 4.4; 424/401
See application file for complete search history.

(56) References Cited

U.S. PATENT DOCUMENTS

| 2,183,084 A | 12/1939 | Reynolds |
| 2,886,446 A | 5/1959 | Kramer et al. |
| 3,137,630 A | 6/1964 | Hecker et al. |
| 3,137,670 A | 6/1964 | Maneri |
| 3,932,609 A | 1/1976 | Rosenstreich et al. |
| 4,209,417 A | 6/1980 | Whyte |
| 4,251,195 A * | 2/1981 | Suzuki et al. ..................... 425/6 |
| 4,422,985 A * | 12/1983 | Morishita et al. ............... 264/4.4 |
| 4,428,869 A | 1/1984 | Munteanu et al. |
| 4,434,153 A | 2/1984 | Urquhart et al. |
| 5,089,269 A | 2/1992 | Noda et al. |
| 5,208,038 A | 5/1993 | Gressani et al. |
| 5,726,138 A | 3/1998 | Tsaur et al. |
| 5,753,244 A | 5/1998 | Reynolds et al. |
| 5,961,990 A | 10/1999 | Delrieu et al. |
| 6,045,813 A | 4/2000 | Ferguson et al. |
| 6,248,268 B1 * | 6/2001 | Cook ............................. 264/12 |
| 6,251,409 B1 | 6/2001 | Hegyi et al. |

FOREIGN PATENT DOCUMENTS

| DE | 199 37 830 | 2/2001 |
| DE | 199 62 350 | 6/2001 |
| EP | 0 254 447 | 1/1988 |
| EP | 0 316 054 | 5/1989 |
| EP | 0 389 700 | 10/1990 |
| EP | 0 412 865 | 2/1991 |
| EP | 0 900 558 | 3/1999 |
| GB | 490001 | 8/1938 |
| GB | 655592 | 7/1951 |
| GB | 887901 | 1/1962 |
| JP | 1-193216 | 8/1989 |
| JP | 2-117610 | 5/1990 |
| JP | 6-154587 | 6/1994 |
| JP | 6-509502 | 10/1994 |
| JP | 7-304651 | 11/1995 |
| JP | 10-24258 | 1/1998 |
| JP | 11-29433 | 2/1999 |
| JP | 2000-239147 | 9/2000 |
| JP | 2001-187710 | 7/2001 |
| WO | WO 96/29979 | 10/1996 |
| WO | WO 98/08601 | 3/1998 |
| WO | WO 99/36477 | 7/1999 |
| WO | WO 99/52500 | 10/1999 |
| WO | WO 99/59541 | 11/1999 |

OTHER PUBLICATIONS

Dubowoj et al., EP 0 900 558, 1999, English Translation.
Lipochemicals, Retrieved from the Internet URL:http://www.lipochemicals.com/doc/i_1.htm XP-002203291, pp. 1-4. "Targeted Delivery Syt+Stems", Jun. 21, 2002.

* cited by examiner

*Primary Examiner* — Gina C Yu
(74) *Attorney, Agent, or Firm* — Oblon, Spivak, McClelland, Maier & Neustadt, L.L.P.

(57) ABSTRACT

A skin cosmetic composition comprising: a hydrogel particle comprising a non-crosslinked hydrogel containing an oil component therein dispersed in an aqueous medium; a hydrogel particle comprising a non-crosslinked hydrogel containing an oil component therein; and a process for preparing a hydrogel particle comprising the steps of discharging an oil component-emulsified or dispersed solution prepared by dissolving a non-crosslinked hydrogel in an aqueous solution, with vibration from an orifice to form droplets; and cooling the droplets to solidify.

20 Claims, No Drawings

SKIN COSMETIC COMPOSITION

BACKGROUND OF THE INVENTION

1. Field of the Invention

The present invention relates to a skin cosmetic composition having excellent utility, which gives sufficient moisturizing effects while being free from tackiness and having refreshing feeling. More specifically, the present invention relates to a skin cosmetic composition which can be used as lotion and the like.

The present invention also relates to a hydrogel particle and a process for preparing the same. More specifically, the present invention relates to a hydrogel particle in which an oil component is dispersed and which can be applied to cosmetics, pharmaceuticals, quasi-drug, foods and the like.

2. Discussion of the Related Art

Conventionally, as an aqueous cosmetic composition containing an oil component for the purposes of giving moisturizing effect, there have been known aqueous cosmetic compositions having an emulsion form, a solubilized form or a double-layer form.

The aqueous cosmetic composition having an emulsion form (milky lotion) can supplement an oily component to skin. However, the emulsion sometimes becomes unstable when a component which affects emulsion stability, such as an electrolyte is added to the composition. As a result, there are some defects such that moisturizing effects are impaired.

The aqueous cosmetic composition having a solubilized form (lotion) imparts moisturizing effects to skin to some extent. However, there are some defects in the composition such that the amount of an oil to be used in the composition should be relatively reduced, so that sufficient moisturizing effects are not maintained.

Also, the aqueous cosmetic composition having a double-layer form comprising an aqueous phase and an oil phase separated from each other is excellent in moisturizing effects, and their effects can be maintained. However, there are some defects in the composition such that the selection of their components used in the oil phase and the aqueous phase and the control of their compositional ratio would be difficult for giving a homogeneous dispersion only by shaking the composition upon use, and for recovering the original double layer by allowing it to stand. Especially, since a liquid oil is used in the composition in a large amount as a component for the oil phase, there are some defects in the composition such that the user's feel is unpleasant, and that the composition is applied inhomogeneously upon use, so that the composition is not good in fitness for the skin.

Under the above circumstances, there have been proposed various capsule-containing cosmetic compositions having both moisturizing effects and its maintaining effects, while exhibiting the characteristics of the aqueous cosmetic composition having a solubilized form (lotion).

For instance, there have been proposed a cosmetic composition containing an oil-in-water type (hereinafter referred to as O/W type) emulsion-incorporating capsule, wherein the capsule has a shell containing calcium alginate, the content of which is 0.1 to 1.0% by weight based on the entire amount of the capsule (Japanese Patent Laid-Open No. Hei 2-117610); an alginate capsule-containing cosmetic composition in which a part of the alginates is existing in the form of a polyvalent metal salt containing a barium salt as an essential component, wherein the capsules exist in the outer phase comprising an aqueous solution of carboxyvinyl polymer, the pH of which is adjusted (Japanese Patent Laid-Open No. Hei 11-29433); and a water-containing cosmetic composition comprising soft capsules or spheres, the substrate of which is agar (Japanese Patent Laid-Open No. Hei 1-193216).

The alginate-based capsule is prepared by reacting a water-soluble alginate with a water-soluble calcium salt to form a water-insoluble calcium alginate. Therefore, the incorporation of a surfactant, a water-soluble polymer, or an inorganic salt, those containing a di- or more valent metal ion, into the capsule is restricted. The stability of the alginate capsule depends upon pH, and the capsule is stable in a specified acidic region. However, the capsule is dissolved and broken in an alkaline region. In addition, if the washing of the polyvalent metal ions used in the curing reaction is insufficient after the preparation of the capsule, in the case where the outer phase comprises an aqueous medium containing a thickener not having enough tolerance against a salt, the viscosity of the aqueous medium is reduced by the remaining polyvalent metal ions, so that the dispersion of the capsule becomes inhomogeneous, thereby making it unfavorable in properties and appearance. Therefore, the aqueous medium is limited to those containing a thickener such as a polysaccharide which would not affect the aqueous medium, so that refreshing user's feel free from tackiness is difficult to be obtained.

The soft capsule, the substrate of which is agar necessitates agar in a high concentration in order to form a shell. Therefore, there are some defects such that some residue of agar remains on skin when the soft capsule is applied to the skin, causing unpleasant feeling. In addition, as a process for preparing a soft capsule, there has been known a process disclosed in Japanese Patent Laid-Open No. Hei 1-193216 mentioned above. However, it is difficult to obtain particles having high monodispersibility efficiently.

An object of the present invention is to provide a skin cosmetic composition in which particles are dispersed or suspended in a liquid medium, showing good appearance, being excellent in storage stability without allowing the particles to float or precipitate in the liquid medium with the passage of time, being smooth on skin when applied thereto, and having no residue of particles on the skin, thereby favorably exhibiting effects based on the ingredients.

Another object of the present invention is to provide a skin cosmetic composition in which specified particles are dispersed or suspended in a flowable substrate having a relatively low viscosity, and the visible particles give pretty impression, and the ingredients can be uniformly spread over the skin when the cosmetic composition is applied thereto, thereby realizing refreshing feel without tackiness.

A still another object of the present invention is to provide a hydrogel particle and a process for efficiently preparing the same, whereby the hydrogel particle having high sphericity and excellent monodispersibility, having an oil component therein stably dispersed in high content, being applied to cosmetics, pharmaceuticals, quasi-drug, and foods.

These and other objects of the present invention will be apparent from the following description.

SUMMARY OF THE INVENTION

According to the present invention, there are provided:
(1) a skin cosmetic composition comprising:
(A) a hydrogel particle comprising a non-crosslinked hydrogel containing an oil component therein dispersed in
(B) an aqueous medium;
(2) a hydrogel particle comprising a non-crosslinked hydrogel containing an oil component therein;

(3) a process for preparing a hydrogel particle comprising the steps of:

discharging an oil component-emulsified or dispersed solution prepared by dissolving a non-crosslinked hydrogel in an aqueous solution, with vibration from an orifice to form droplets; and cooling the droplets to solidify; and (4) a skin cosmetic composition comprising visibly recognizable particles having an average particle diameter of 0.1 to 5 mm and an aqueous medium having a viscosity of 300 to 500 mPa·s at 25° C. as determined by Brookfield viscometer and a specific gravity of 0.7 to 2.0, the visibly recognizable particles being dispersed in the aqueous medium.

DETAILED DESCRIPTION OF THE INVENTION

The term "non-crosslinked hydrogel" as referred to herein means a gel comprising water as a dispersion medium, in which the formation of the gel is based upon not a crosslinking reaction via potassium ions or calcium ions but a heat-reversible sol-gel transformation. The polymer material which forms the above gel includes, for instance, agar, gelatin and the like, and these materials can be used alone or in admixture.

The dissolution temperature of the agar in water is generally not less than 75° C., principally 75° to 90° C. The gelation temperature of an agar aqueous solution upon cooling is 30° to 45° C.

Examples of the non-crosslinked hydrogel include agar and gelatin. These non-crosslinked hydrogels can be used alone or in admixture thereof. Among them, agar is preferable. The gel strength of the agar is preferably not more than 68.6 kPa (700 g/cm$^2$), more preferably 19.6 kPa (200 g/cm$^2$) to 63.7 kPa (650 g/cm$^2$), from the viewpoint of texture upon use.

The gel strength is determined by NIKKAN-SUI-SIKI Method. According to the NIKKAN-SUI-SIKI Method, the gel strength is determined by applying a load to a gel, being prepared by allowing a 1.5% by weight agar aqueous solution to stand at 20° C. for 15 hours to harden, with a NIKKAN-SUI-SIKI gel strength measuring device commercially available from KIYA SEISAKUSHO Co., Ltd. to obtain the maximum weight (g) per 1 cm$^2$ surface area of the gel when the gel endures the load for 20 seconds at 20° C.

The term "hydrogel particle" as referred to herein means an approximately spherical particle made of a hydrogel, and does not include a so-called capsule composed of a shell and a core material. One of the great features of the hydrogel particle of the present invention resides in that the non-crosslinked hydrogel forms a continuous phase, and an oil component is contained therein as a dispersion phase.

The non-crosslinked hydrogel particle (A) is a particle having a spherical shape, prepared by incorporating an oil component usually used in cosmetics into a sol prepared by dissolving a polymer for forming a non-crosslinked hydrogel in water, and subjecting the gel to a heat-reversible sol-gel transformation.

The content of the continuous phase in the hydrogel particle is preferably 40 to 99% by weight, more preferably 40 to 92.5% by weight, still more preferably from 60 to 90% by weight, especially preferably 60 to 80% by weight, from the viewpoint of preventing the breaking during washing of the hydrogel particle and formulating it into cosmetics.

The content of the polymer for forming the non-crosslinked hydrogel in the continuous phase is preferably 0.25 to 5.1% by weight, more preferably 0.75 to 2.0% by weight, from the viewpoints of giving excellent texture upon use and preventing the breaking during washing of the hydrogel particle and formulating it into cosmetics.

Accordingly, the content of the non-crosslinked hydrogel-forming substance in the hydrogel particles is preferably 0.1 to 5.0% by weight, more preferably 0.3 to 2.0% by weight.

On the other hand, as the oil component, various fats and oils such as solid fats and liquid oils can be used. In a skin cosmetic composition, the oil component is added for the purpose of skin care. The skin care can be carried out by giving skin moisturizing properties, and softening and smoothening the skin, thereby improving the texture of the skin.

The oil component includes, for instance, liquid oils such as hydrocarbon oils, ester oils and plant oils; solid to semi-solid oils such as hardening oils, solid paraffins, Vaseline, and ceramides and analogs thereof, such as natural ceramides of Types I to VI, ceramide derivatives having sugar moiety, and aliphatic amide derivatives of ceramide analogs such as N-(2-hydroxy-3-hexadecyloxypropyl)-N-2-hydroxyethylhexadecanamide and N-(2-hydroxy-3-hexadecyloxypropyl)-N-2-hydroxyethyldecanamide, higher alcohols (14 to 22 carbon atoms), higher fatty acids (12 to 22 carbon atoms), glyceride, ethylene glycol di-fatty acid esters (number of carbon atoms of the fatty acid moiety being 12 to 36), and dialkyl ethers (total number of carbon atoms: 12 to 36); oil-soluble vitamins; and liquid, semisolid or solid silicones. The oil-soluble vitamins include vitamin A, vitamin E, vitamin D and derivatives thereof, such as fatty acid esters of vitamin A (palmitate, acetate and the like), fatty acid esters of vitamin E (acetate, linoleate and the like) and the like. The silicones include, for instance, silicone oils such as dimethyl polysiloxane, methylphenyl polysiloxane, octamethyl cyclotetrasiloxane, decamethyl cyclopentasiloxane and methyl hydrogenpolysiloxane; dimethyl polysiloxanes having a high polymerization degree; silicone resins; silicone rubbers; silicone beads; amino-modified silicones; alkyl-modified silicones; and the like.

The term "solid fat" as referred to herein means an oil component having a melting point of not less than 35° C. The term "liquid fat" as referred to herein means an oil component having a melting point of less than 35° C. The melting point of the oil component is a value as determined by differential scanning calorimetry (hereinafter referred to as DSC).

It is preferable that the oil component contains a solid fat, or a solid fat and a liquid oil, from the viewpoint of preventing leakage of the oil component from the hydrogel particle during the high-temperature storage.

The melting point of the oil component is preferably not less than 35° C., more preferably 40° to 90° C., still more preferably 50° to 90° C., especially preferably 60° to 80° C.

Among them, the melting point of the solid fat being determined by DSC is preferably 40° to 120° C., more preferably 50° to 100° C., especially preferably 50° to 90° C.

The content of the solid fat in the oil component is preferably 1 to 80% by weight, more preferably 6 to 80% by weight, still more preferably 10 to 70% by weight, most preferably 19 to 70% by weight, from the viewpoint of suppressing the leakage of the oil component from the hydrogel particle and from the viewpoint of giving skin smoothness.

The content of the liquid oil in the oil component is preferably 20 to 99% by weight, more preferably 20 to 94% by weight, still more preferably 30 to 90% by weight, most preferably 30 to 81% by weight, from the viewpoint of suppressing the leakage of the oil component from the hydrogel particle and from the viewpoint of giving skin smoothness.

In addition, there can be properly added to a continuous phase or dispersed phase of the hydrogel particle sugars, polyhydric alcohols, surfactants, polymers, ultraviolet shielding agents, UV radiation absorbing substances, perfumes, colorants, preservatives, powders and the like, as occasion demands. The polymers include, for instance, acrylic, styrenic, ether-based, ester-based, or silicone-based polymer emulsions or suspensions.

The colorants include water-insoluble pigments, oil-soluble dyes, vat dyes, lake dyes and the like. The pigments include, for instance, inorganic pigments such as carbon black, talc, kaolin, mica, mica titanium, red oxide, bismuth oxychloride, magnesium silicate, titanium oxide and iron oxide; and organic pigments such as Red 202, Red 204, Red 205, Red 206, Red 219, Red 228, Red 404, Yellow 205, Yellow 401, Orange 401 and Blue 404. The oil-soluble dyes include, for instance, Red 505, Red 501, Red 225, Yellow 404, Yellow 405, Yellow 204, Orange 403, Blue 403, Green 202, Violet 201 and the like. The vat dyes include, for instance, Red 226, Blue 204, Blue 201 and the like. The lake dyes include, for instance, those prepared by laking various acidic dyes with aluminum or barium. These colorants can be used alone or in admixture thereof.

The content of the oil component in the hydrogel particle (A) is preferably 1 to 60% by weight, more preferably 10 to 60% by weight, still more preferably 20 to 40% by weight, from the viewpoints of the texture of the particle upon use and effects such as moisturizing.

The average particle diameter of the hydrogel particle (A) is preferably 0.005 to 10 mm, more preferably 0.1 to 10 mm, still more preferably 0.5 to 5 mm, especially preferably 1.15 to 5 mm, from the viewpoints of easiness in the preparation and productivity. The average particle diameter of the hydrogel particle (A) means a weight-average particle diameter determined by classifying the hydrogel particles using screens having various sieve-openings and calculating the weight-average particle diameter in accordance with a screening method. Specifically, 100 g of the hydrogel particles (A) are subjected to wet classification in water by stacking screens with sieve-openings of 3.35 mm, 2.80 mm, 2.36 mm, 2.00 mm, 1.70 mm, 1.40 mm, and 1.00 mm. The weight-average particle diameter is determined from a sieve-opening of each screen (mm) and each weight percentage by weighing the particles remaining on each screen and the particles passing through 1.00 mm sieve.

In the hydrogel particles (A), the weight ratio of the water contained therein to the polymer constituting the hydrogel [water/polymer] is preferably 25 to 1000, more preferably 50 to 500, from the viewpoints of making the particles unbreakable by mechanical forces such as stirring and washing during the preparation of the hydrogel particles and the addition to a cosmetic composition, and giving excellent texture upon use and an appropriate disintegration properties.

The shape of the hydrogel particle is not limited to specified ones, and it is preferable that the hydrogel particle has a shape corresponding to the rotation symmetry. The term "shape corresponding to the rotation symmetry" means a shape produced by rotating a figure formed by a continuous curve on its virtual axis, and does not include a shape having a plane surface such as a trigonal pyramid or a cylinder. It is more preferable that the shape of the hydrogel particle is spherical, from the viewpoint of appearance.

It is desired that the ratio of the longest diameter to the shortest diameter (longest diameter/shortest diameter) of the particle is not more than 1.7, preferably not more than 1.5, more preferably not more than 1.2, from the viewpoint of appearance.

In addition, it is desired that hydrogel particles having a ratio of the longest diameter to the shortest diameter (longest diameter/shortest diameter) of not more than 1.7 are contained in the hydrogel particles in the content of not less than 80% by weight, preferably not less than 90% by weight, from the viewpoint of appearance. The longest diameter and the shortest diameter are determined by the method for determining sphericity described in Examples given below.

In addition, it is desired that the breaking intensity of the hydrogel particle is 2 to 40 kPa, preferably 5 to 25 kPa, from the viewpoint of improving texture upon use, and that the Young's modulus of the hydrogel particle is 10 to 150 kPa, preferably 30 to 100 kPa.

When the breaking intensity is not less than 2 kPa, the hydrogel particle is less breakable during washing of the hydrogel particle and formulating the hydrogel particle into a cosmetic. When the breaking intensity is not more than 40 kPa, the hydrogel particle is extensible on skin and suited for the skin.

When the Young's modulus is not less than 10 kPa, the hydrogel particle is less breakable during washing of the hydrogel particle and formulating the hydrogel particle into a cosmetic, and the oil component dispersed in the particles is less likely to leak out from the hydrogel particle during washing. Also, when the Young's modulus is not more than 150 kPa, the hydrogel particle is extensible on skin.

The breaking intensity and the Young's modulus are determined in accordance with the determination methods described in Examples given below.

For instance, the hydrogel particle (A) containing an oil component can be prepared as follows.

First, a water-soluble polymer for forming a non-crosslinked hydrogel such as agar or gelatin is dispersed in ion-exchanged water, and the mixture is sufficiently stirred and dissolved at a temperature of not less than the dissolving temperature, to give a sol. Thereafter, an oil component is mixed with the sol at a temperature of not less than the gelation temperature, to give an O/W type dispersion.

It is preferable that the average particle diameter of the oil component is smaller than the particle diameter of the hydrogel. Also, it is more preferable that the average particle diameter is not more than 10% of the particle diameter of the hydrogel. However, it is desired that the average particle diameter of the oil component is preferably not more than 500 µm, more preferably not more than 100 µm, still more preferably not more than 50 µm, especially preferably not more than 20 µm, from the viewpoint that the hydrogel particles can be smoothly extended on the skin. In addition, the average particle diameter of the oil component is preferably not less than 0.5 µm, more preferably not less than 4 µm, still more preferably not less than 5 µm, especially preferably not less than 10 µm, from the viewpoint of fitting of the oil component to the skin. In considerations of these viewpoints, the average particle diameter of the oil component is preferably from 0.5 to 500 µm, more preferably from 4 to 100 µm, still more preferably from 5 to 50 µm, especially preferably from 10 to 20 µm.

The average particle diameter of the oil component is intended to mean a volume-average particle diameter obtained by measuring each particle diameter of the oil components contained in the dispersion before the preparation of the hydrogel particle with a laser diffraction/scattering type particle size analyzer (commercially available from Horiba, LTD. under the Model No. LA-910), and obtaining an average from the particle diameters as shown in Examples given below.

It is preferable that the oil component contains an emulsifying agent or a dispersing agent, so that the oil component can stably exist in an emulsion or dispersion during the preparation of the O/W dispersion.

The emulsifying agent and the dispersing agent include at least one compound selected from the group consisting of polymer emulsifying-dispersing agents, nonionic surfactants, anionic surfactants, cationic surfactants and amphoteric surfactants. It is desired that the concentration of the emulsifying agent and/or the dispersing agent in the dispersion is usually 0.001 to 20% by weight, preferably 0.005 to 10% by weight, more preferably 0.1 to 5% by weight.

Among the emulsifying agents and the dispersing agents, a combined use of at least one surfactant selected from the group consisting of nonionic surfactants, anionic surfactants, cationic surfactants and amphoteric surfactants, with the polymer emulsifying-dispersing agent is preferable, more preferably a combined use of the nonionic surfactant and the polymer emulsifying-dispersing agent, still more preferably a single use of the polymer emulsifying-dispersing agent, from the viewpoint of spreadability on skin and handling during washing and formulating into a cosmetic. When the polymer emulsifying-dispersing agent is used, the tackiness caused by the surfactant can be reduced when the particles are applied to skin, since the amount of the surfactant can be reduced or omitted.

The polymer emulsifying-dispersing agent includes, for instance, a copolymer of acrylic acid and alkyl methacrylate (commercially available from B.F. Goodrich under the trade name of PEMULEN, and the like); a composite prepared from an amphoteric polymer and a higher fatty acid as disclosed in Japanese Patent Laid-Open No. Hei 7-100356; water-soluble amphipathic polymer electrolytes as disclosed in Japanese Patent Laid-Open Nos. Hei 8-252447 and Hei 9-141079; water-soluble crosslinked amphipathic polymer electrolytes as disclosed in Japanese Patent Laid-Open Nos. Hei 9-141080 and Hei 9-141081; synthetic polymers such as acrylic acid-based copolymers, polyvinyl pyrrolidones, polyvinyl alcohols and derivatives thereof, polyacrylamides and ethylene oxide adducts of alkylphenol formaldehyde condensates as disclosed in Japanese Patent Laid-Open No. Hei 10-53625; and natural polymers such as guar gum, karaya gum, tragacanth gum, gum arabic, arabinogalactan and casein. Among them, the copolymer of acrylic acid and alkyl methacrylate, the acrylic acid-based copolymers (Carbopol) and the polyvinyl alcohols are preferable, from the viewpoint of reduced tackiness.

As the nonionic surfactants, the anionic surfactants, the cationic surfactants and the amphoteric surfactants, those usually used for cosmetics can be used alone or in admixture thereof.

The particle can be prepared from the dispersion thus obtained by a general dropping method or stirring method.

The dropping method is a process for preparing a particle, utilizing the technique such that a liquid obtained by discharging a dispersion from an orifice is formed into a droplet by its surface or interfacial tension. The droplet formed by the dropping method is cooled to solidify in the atmosphere or in liquid, to give a particle.

In the dropping method, a droplet can be formed in the atmosphere, or in liquid. When the droplet is formed in the liquid, the droplet can be formed in a stand-still liquid. It is preferable that the droplet is formed in the liquid stream having a downward flow, an upward flow or a cocurrent flow with a pipe for forming a droplet. The end surface of the pipe can exist either in the atmosphere or in the liquid. When the droplet is formed in the liquid, it is preferable that the end surface exists in the liquid.

The dispersion prepared in the above method is heated to a temperature of not less than the gelation temperature, and the dispersion is discharged from the orifice into the atmosphere such as air or liquid in the form of a droplet or a liquid column. During discharging, the liquid column is formed into a droplet by its surface tension, and further cooled to solidify. In this case, when the discharging rate is fast, the liquid column is cooled to solidify in some cases before the formation of a droplet. Therefore, it is preferable that the discharging rate is not so fast. However, when a vibration is applied to the dispersion, the formation of the liquid column into a droplet is accelerated, so that the production efficiency is improved. In addition, when a vibration is applied, since the size of the formed droplet becomes even, the monodispersibility of the particles is improved. Therefore, in order to improve the production efficiency and the monodispersibility of the particles, it is preferable that the vibration is applied to the dispersion. The method of applying vibration is not limited. Examples of the method include a method of applying vibration to an orifice, thereby applying vibration to a liquid column; a method of applying vibration to a dispersion to be discharged from an orifice before discharging; a method of applying vibration to a liquid column discharged from an orifice by pulsating flow of a cooling liquid; a method of applying vibration to a liquid column discharged from an orifice by a vibrating ring set around the liquid column; and the like.

Among the above methods, in order to efficiently carry out the formation of particles of the dispersion, the method of applying vibration to a dispersion to be discharged from an orifice before discharging is preferable.

The frequency of the vibration can be properly selected depending upon the discharging rate, i.e. linear velocity and the liquid viscosity. The frequency applied is not limited, and the frequency is preferably 1 to 2000 Hz, more preferably 5 to 200 Hz.

When the droplet is formed in the liquid, the droplet can be formed in a stand-still liquid. It is preferable that the droplet is formed in the liquid stream having downward flow, an upward flow or a cocurrent flow with a pipe for forming a droplet. The flow rate of the liquid in the liquid stream is preferably 0.8 to 5 times that of the dispersion. It is more preferable that the flow rate is 0.8 to 2 times that of the dispersion, from the viewpoint of making the size of the formed droplets even. In addition, the end surface of the pipe can be positioned in either the atmosphere or the liquid. When the droplet is formed in the liquid, it is preferable that the end surface exists in the liquid.

The orifice diameter is not limited to specified ones. It is desired that the orifice diameter is usually 0.1 to 5 mm. The temperature of the dispersion discharged from the orifice is not limited to specified ones as long as the temperature of the dispersion is not less than the gelation temperature. It is desired that the temperature of the dispersion is usually 40° to 100° C.

It is desired that the temperature of the gas or liquid for solidifying the dispersion is not more than the gelation temperature, preferably not more than 40° C., more preferably not more than 20° C.

The stirring method is a process for preparing a particle, using a technique such that a dispersion is added to a liquid being substantially immiscible with the dispersion and temperature-controlled to not less than the gelation temperature of the non-crosslinked hydrogel, the dispersion is formed into fine particles by shearing force with stirring, and the fine particles are formed into a droplet by its surface tension. The droplet formed by the stirring method is cooled to solidify in a liquid substantially immiscible with the dispersion, to give a solid particle.

The temperature of the dispersion as discharged of the dispersion is not limited to specified ones. It is preferable that the temperature of the dispersion is not less than the gelation temperature of the non-crosslinked hydrogel and not more than 100° C. It is desired that the temperature of the dispersion is higher than the gelation temperature by not less than 10° C., preferably higher than the gelation temperature by not less than 20° C., from the viewpoint of easiness in preparing a spherical particle having excellent appearance. It is desired that the upper limit of the temperature is 100° C., that is, a boiling point of water.

The viscosity of the dispersion can be determined by a Brookfield viscometer. The viscosity of the dispersion is not limited to specified ones. It is desired that the viscosity of the dispersion at discharging of the dispersion is usually 0.1 to 1000 mPa·s, preferably 1 to 800 mPa·s at the temperature of discharging of the dispersion.

In the skin cosmetic composition of the present invention, the hydrogel particle (A) is dispersed in an aqueous medium (B) as a substrate for a cosmetic composition.

It is desired that the content of the hydrogel particle (A) in the skin cosmetic composition is 1 to 40% by weight, preferably 5 to 30% by weight, from the viewpoints of appearance and physical properties.

In the present invention, the aqueous medium (B) is not limited to specified ones, as long as the hydrogel particle (A) can be stably and homogeneously dispersed therein, without precipitating or floating. The aqueous medium can be used in any forms such as transparent or semitransparent aqueous solutions, O/W type emulsion or gel, and the like. The hydrogel particle (A)-dispersed skin cosmetic composition can be designed in the forms of lotion, milky lotion, cream, gelated cosmetic and the like.

In order to impart desired liquid properties to the aqueous medium (B), a water-soluble thickener can be contained in the aqueous medium (B). As the water-soluble thickener, there can be used, for instance, a water-soluble polymer, clay, and the like. The amount of the water-soluble thickener can be selected, so that the viscosity (Brookfield viscometer at 25° C.) of the aqueous medium (B) becomes appropriate for the viscosity and specific gravity of the skin cosmetic composition.

The viscosity of the aqueous medium is 300 to 5000 mPa·s at 25° C., preferably 500 to 3000 mPa·s, from the viewpoints of homogenous dispersibility of the particles, appearance and users' feel, especially impression and users' feel as a lotion.

The specific gravity of the aqueous medium is 0.7 to 2.0, preferably 0.8 to 1.5, from the viewpoints of the monodispersibility of the particles and the users' feel as cosmetics.

In the present invention, the aqueous medium is preferably a transparent or semitransparent flowable liquid having a viscosity of 300 to 5000 mPa·s at 25° C. and a specific gravity of 0.7 to 2.0, from the viewpoints of giving the cosmetic composition flowability especially useful as lotion, and transparency in appearance. Further, since the particles to be dispersed in the aqueous medium are stably dispersed and suspended in the aqueous medium, the dispersion is excellent in appearance, and also gives refreshing feel.

The phrase "the aqueous medium is transparent or semitransparent" as used herein means that the light transmittance is not less than 30%.

The aqueous polymers include, for instance, plant-based polymers such as gum arabic, tragacanth gum, galactan, carob gum, guar gum, karaya gum, carrageenan, pectin, agar, quince seed gum (marmelo), starches (rice, Indian corn, white potato, wheat), and algae colloids (brown algae extract); microorganism-based polymers such as dextran, succinoglucan and pullulan; animal-based polymers such as collagen, casein, albumin and gelatin; modified starches such as carboxymethyl starch and methylhydroxypropyl starch; modified celluloses such as methyl cellulose, ethyl cellulose, methylhydroxypropyl cellulose, hydroxyethyl cellulose, sodium cellulose sulfate, hydroxypropyl cellulose and sodium carboxymethyl cellulose; alginates such as sodium alginate and propylene glycol alginate; vinyl polymers such as polyvinyl methyl ether, and carboxymethyl polymer (commercially available from BF Goodrich under the trade name of CARBOPOL941, and the like); polyoxyethylene polymers; polyoxyethylene-polyoxypropylene copolymer; acrylic polymers such as sodium polyacrylate, polyethyl acrylate and polyacrylamide; polyethyleneimine; cationic polymers; inorganic compounds such as bentonite, aluminum magnesium silicate, hectorite and silicic acid anhydride; cationic crosslinked copolymers disclosed in Japanese Patent Laid-Open No. Hei 11-71435; water-soluble polysaccharides disclosed in Japanese Patent Laid-Open Nos. 9-235301 and 10-25301; and the like.

The cationic crosslinked copolymers disclosed in Japanese Patent Laid-Open No. Hei 11-71435 are copolymers having a cationic group and a crosslinked structure in its molecule. The cationic crosslinked copolymers include, for instance, a cationic crosslinked copolymer prepared by copolymerizing at least one cationic group-containing vinyl monomer [hereinafter referred to as monomer $(a_1)$], at least one amide-group containing vinyl monomer [hereinafter referred to as monomer $(a_2)$], and at least one crosslinkable vinyl monomer having not less than two vinyl groups in its molecule [hereinafter referred to as monomer $(a_3)$] [hereinafter referred to as copolymer (A)], which give the aqueous medium (B) favorable thixotropy.

Preferable concrete examples of the monomer $(a_1)$ include acid-neutralized compounds of monomers having amino group such as dimethylaminoethyl (meth)acrylate, diethylaminoethyl (meth)acrylate, dimethylaminopropyl (meth)acrylamide, and diethylaminopropyl (meth)acrylamide, or quaternary ammonium salts of these monomers prepared by quaternarizing the monomers with a quaternalizing agent; dimethyldiallylammonium chloride; and the like.

Preferable concrete examples of the monomer $(a_2)$ include N,N-di-substituted (meth)acrylamide such as N,N-dimethyl (meth)acrylamide and N,N-diethyl (meth)acrylamide; N-methyl (meth)acrylamide, N-n-propyl (meth)acrylamide, N-t-butyl (meth)acrylamide, N-(meth)acryloylmorpholine, N-vinylpiperidone, N-vinylpyrrolidone and the like. Among them, from the viewpoint of improving the user's feel, N,N-di-substituted (meth)acrylamide is preferable, and N,N-dimethyl (meth)acrylamide and N,N-diethyl (meth)acrylamide are more preferable.

Preferable concrete examples of the monomer $(a_3)$ include (meth)acrylates of polyhydric alcohols or unsaturated alcohols; bis(meth)acrylamide, divinyl compounds, polyallyl compounds; and the like. Among them, ethylene glycol di(meth)acrylate, polyethylene glycol di(meth)acrylate, pentaerythritol tetra(meth)acrylate, allyl ethers of pentaerythritol, vinyl (meth)acrylate and allyl (meth)acrylate are especially preferable.

As the cationic crosslinked copolymers, copolymers made of preferably exemplified monomers $(a_1)$ to $(a_3)$ are preferable. Especially, the combination of dimethylaminoethyl (meth)acrylate/N,N-dimethyl (meth)acrylamide/polyethylene glycol di(meth)acrylate is preferable, from the viewpoint of thixotropy of the aqueous medium (B).

The content of the monomer ($a_3$) in the total monomers is preferably 0.002 to 5% by mol, especially 0.002 to 3% by mol, more especially 0.002 to 1% by mol. When the content of the monomer ($a_3$) is within the above range, the viscosity of the aqueous medium (B) containing the copolymer (A) is suitable, thereby giving soft texture and smoothness.

It is preferable that the pH of the aqueous medium (B) is 4 to 11, especially 4 to 6, from the viewpoint of being less irritant to skin.

The method of dispersing and suspending the particles in the aqueous medium (B) is not limited to specified ones, as long as the particles can be stably and homogeneously dispersed without precipitating the particles or allowing the particles to float. Examples of the method include a method comprising adding an aqueous dispersion of particles to the previously prepared aqueous medium (B), and stirring the mixture to homogeneously disperse the particles in the aqueous medium; and the like.

To the aqueous medium (B), there can be added those components usually used in cosmetic compositions, such as ultraviolet shielding agents, UV radiation absorbing substances, moisturizing agents, alcohols, vitamins, hydroxycarboxylic acids and salts thereof, preservatives, water-soluble polymers, coloring matters, perfumes, antioxidants and the like in proper amounts. The water-soluble vitamins include niacin, vitamin $B_2$, vitamin $B_6$, vitamin C and biotin. The hydroxycarboxylic acids are exemplified by glycolic acid, lactic acid, salicylic acid and the like.

As described above, since the non-crosslinked hydrogel is used in the hydrogel particle of the present invention, the compositional restriction is eliminated, and at the same time the hardness of the ingredients in the particle becomes uniform, so that the hardness of the surface is not greater than that in the inner part of the particle, as in the case of crosslinked hydrogel particles. Therefore, the particle can be smoothly broken with fingers when applied to the skin. Furthermore, since there is no shell portion as in the case of a core-shell capsule, the hydrogel particle is easily broken and spread over the skin, and no residue of particles exists on the skin.

Another embodiment of the present invention, that is, a skin cosmetic composition comprising visibly recognizable particles having an average particle diameter of 0.1 to 5 mm and a specified aqueous medium, the visibly recognizable particles being dispersed in the aqueous medium is explained. The term "visibly recognizable" as referred to herein means that non-transparent or colored particles exist in the transparent or semitransparent aqueous substrate, so that the presence of the particles can be visibly recognized. In the present invention, since the above particles are employed, the particles can be visibly recognized with naked eyes, and the number of the particles can be counted, even when the particles are dispersed in a transparent or semitransparent aqueous substrate.

The visibly recognizable particles may be any of inorganic particles and organic particles. Also, the visibly recognizable particles may be granulated ones of such particles.

Examples of the inorganic particles and organic particles include inorganic powders such as talc, mica, kaolin, muscovite, synthetic mica, phlogopite, biotite, Lithia mica, vermiculite, magnesium carbonate, calcium carbonate, diatomaceous earth, magnesium silicate, calcium silicate, aluminum silicate, barium silicate, strontium silicate, metal salts of tungstic acid, hydroxyapatite, hydrated silicic acid, magnesium oxide, bentonite, zeolite, ceramic powder and aluminum hydroxide; organic powders such as nylon powder, polyethylene powder, polymethyl benzoguanamine powder, polymethyl methacrylate powder, polytetrafluoroethylene powder, fine crystalline cellulose, rice starch and lauroyllysine; powders of metal salts of surfactants such as calcium stearate, zinc stearate, magnesium stearate, magnesium myristate, calcium cetyl phosphate and sodium zinc cetyl phosphate; colored inorganic powders such as titanium oxide, zinc oxide, zirconium oxide, iron oxide (red oxide), iron titanate, iron hydroxide, loess, black iron oxide, carbon black, manganese violet, cobalt violet, chromium oxide, chromium hydroxide, cobalt titanium, ultramarine and Prussian blue; pearly pigments such as titanium oxide-coated mica, titanium oxide-coated bismuth oxychloride, bismuth oxychloride, titanium oxide-coated talc, scale foil and tinted titanium oxide-coated mica; metal powders such as aluminum powder, stainless steel powder and copper powder; powders generally well used in cosmetics; powders prepared by treating the above powders with silicone or a fluorine compound; and the like. In addition, the hydrogel particle formed from agar, gelatin and the like can be preferably used.

The form of the visibly recognizable particles includes granules of powders, and non-encapsulated particles such as gel particles. It is preferable that the shape is spherical, from the viewpoints of appearance and easiness in preparation. Among the particles, those which are breakable with fingers upon applying to the skin are preferable. On the other hand, those particles which are hardly breakable during its preparation, addition to cosmetics, or storage in, for instance, a container are preferable.

In addition, it is preferable that an oily or aqueous conditioning component is contained in the particle. For instance, when the oil component which is separated from the aqueous substrate, or which makes the aqueous substrate white turbid is contained in the particles, the particles can be visibly recognized from the outside, without impairing transparency or semitransparency of the aqueous substrate.

The oily conditioning component is added to the particles because the oily conditioning component gives moisture, and softens or smoothens the skin. As the oily conditioning component, various volatile and non-volatile conditioning components can be used.

The oily conditioning component includes, liquid oils such as hydrocarbon oils, ester oils and plant oils; solid to semi-solid oil agents such as solid paraffins, Vaseline, ceramides, and analogs thereof, such as natural ceramides of Types I to VI, and aliphatic amide derivatives of ceramide analogs such as N-(2-hydroxy-3-hexadecyloxypropyl)-N-2-hydroxyethylhexadecanamide and N-(2-hydroxy-3-hexadecyloxypropyl)-N-2-hydroxyethyldecanamide, higher alcohols (14 to 22 carbon atoms), glyceride, ethylene glycol di-fatty acid esters (number of carbon atoms of the fatty acid moiety being 12 to 36), and dialkyl ethers (total number of carbon atoms: 12 to 36); and liquid, semisolid or solid silicones. The silicones include, for instance, silicone oils such as dimethyl polysiloxane, methylphenyl polysiloxane, octamethyl cyclotetrasiloxane, decamethyl cyclopentasiloxane and methyl hydrogenpolysiloxane; dimethyl polysiloxanes having a high polymerization degree; silicone resins; silicone rubbers; silicone beads; amino-modified silicones; alkyl-modified silicones; and the like.

The aqueous conditioning component includes polyhydric alcohols such as glycerol, 1,3-butanediol, propylene glycol, polyethylene glycol and sorbitol.

It is desired that the content of the conditioning component in the particles is 10 to 60% by weight, preferably 20 to 40% by weight, from the viewpoint of improving texture upon use and moisturizing effects.

EXAMPLES

Preparation Example I-1

Preparation of Hydrogel Particles 1

| (Components) | (% by weight) |
|---|---|
| (1) N-(2-Hydroxy-3-hexadecyloxypropyl)-N-2-hydroxyethylhexadecanamide | 10.0 |
| (2) Fatty acid ester of dipentaerythritol (commercially available from THE NISSHIN OIL MILLS, Ltd. under the trade name of COSMOL 168AR) | 2.5 |
| (3) Polyglyceryl diisostearate (commercially available from THE NISSHIN OIL MILLS, Ltd. under the trade name of COSMOL 42) | 5.0 |
| (4) Methyl polysiloxane (10 mm$^2$/s) | 5.0 |
| (5) Sodium polyoxyethylene lauryl ether phosphate | 0.05 |
| (6) Copolymer of acrylic acid and alkyl methacrylate (commercially available from B. F. Goodrich under the trade name of PEMULEN TR-1) | 0.01 |
| (7) Methyl paraoxybenzoate | 0.3 |
| (8) Agar (commercially available from Ina Shokuhin Kogyo K.K. under the trade name of UP-16) | 1.0 |
| (9) Purified water | Bal. |

(Preparation Method)

The above components (5) to (9) for aqueous phase were mixed and dissolved with heating at 90° C. Next, the components were cooled to 80° C., and a mixture of the above components (1) to (4) for oil phase dissolved beforehand with heating at 80° C. was added thereto, and the mixture was emulsified.

Next, the resulting emulsion was discharged into an oil [methyl polysiloxane (20 mm$^2$/s)] cooled to 10° C. from an orifice having an orifice diameter of 1.5 mm, to give hydrogel particles 1. The resulting hydrogel particles 1 (average particle diameter: 2.0 mm) were separated by filtration, washed and thereafter stored in water.

Preparation Example I-2

Preparation of Hydrogel Particles 2

| (Components) | (% by weight) |
|---|---|
| (1) N-(2-Hydroxy-3-hexadecyloxypropyl)-N-2-hydroxyethylhexadecanamide | 10.0 |
| (2) Fatty acid ester of dipentaerythritol (commercially available from THE NISSHIN OIL MILLS, Ltd. under the trade name of COSMOL 168AR) | 2.5 |
| (3) Polyglyceryl diisostearate (commercially available from THE NISSHIN OIL MILLS, Ltd. under the trade name of COSMOL 42) | 5.0 |
| (4) Methyl polysiloxane (10 mm$^2$/s) | 5.0 |
| (5) Sodium polyoxyethylene lauryl ether phosphate | 0.05 |
| (6) Copolymer of acrylic acid and alkyl methacrylate (commercially available from B. F. Goodrich under the trade name of PEMULEN TR-1) | 0.01 |
| (7) Methyl paraoxybenzoate | 0.3 |
| (8) Sodium alginate | 1.0 |
| (9) Purified water | Bal. |

(Preparation Method)

The above components (5) to (9) for aqueous phase were mixed and dissolved with heating to 90° C. Next, the components were cooled to 80° C., and a mixture of the above components (1) to (4) for oil phase dissolved beforehand with heating at 80° C. was added thereto, and the mixture was emulsified.

Next, the resulting emulsion was added dropwise into a 1% aqueous calcium chloride from an orifice having an orifice diameter of 0.5 mm, to give hydrogel particles 2. The resulting hydrogel particles 2 (average particle diameter: 2.0 mm) were separated by filtration, washed and thereafter stored in water.

Examples I-1 to I-3 and Comparative Examples I-1 to I-6

The constituents of the cosmetic compositions listed in Table 1 other than the hydrogel particles were homogeneously mixed. Thereafter, to the mixture was added the hydrogel particles 1 or the hydrogel particles 2, and the resulting mixture was mixed, to give a cosmetic composition. The resulting cosmetic composition was evaluated for smoothness on skin, residue of particles on skin, sphericity and storage stability by the following methods. The results are shown in Table 1.

(1) Moisturizing Effect

Twenty panel testers conducted sensory evaluation for texture when each cosmetic composition was applied to skin. Its evaluation criteria are as follows:

[Evaluation Criteria]

5: moist

4: slightly moist

3: moderately moist

2: slightly not moist

1: not moist

Next, an average score of the test scores was obtained. When the average score is not less than 4, the texture was evaluated as "○;" when the average score is not less than 2.5 and less than 4, the texture was evaluated as "Δ;" and when the average score is less than 2.5, the texture was evaluated as "x."

(2) Smoothness on Skin

Twenty panel testers conducted sensory evaluation for texture when each cosmetic was applied to skin. Its evaluation criteria are as follows:

[Evaluation Criteria]

5: easily smoothened

4: slightly smoothened

3: moderately smoothened

2: slightly less easily smoothened

1: less easily smoothened

Next, an average score of the test scores was obtained. When the average score is not less than 4, the texture was evaluated as "○;" when the average score is not less than 2.5 and less than 4, the texture was evaluated as "Δ;" and when the average score is less than 2.5, the texture was evaluated as "x."

(3) Residue of Particles on Skin

Twenty panel testers conducted sensory evaluation for texture when each cosmetic was applied to skin. Its evaluation criteria are as follows:

[Evaluation Criteria]
5: no residue of particles
4: not so much residue of particles
3: normal
2: slight residue of particles
1: a lot of residue of particles Next, an average score of the test scores was obtained. When the average score is not less than 4, the texture was evaluated as "◯;" when the average score is not less than 2.5 and less than 4, the texture was evaluated as "Δ;" and when the average score is less than 2.5, the texture was evaluated as "x."

(4) Sphericity

The hydrogel particles used in each example or each comparative example were visually observed to evaluate sphericity. Its evaluation criteria are as follows:

[Evaluation Criteria]
◯: not so much variation in shapes being found
Δ: slight variation in shapes being found
x: variation in shapes being found (5) Storage Stability The cosmetic composition obtained in each example or each comparative example was stored in an atmosphere of 5° C., room temperature or 50° C. for one month. Thereafter, the condition of the cosmetic was visually observed to evaluate storage stability. Its evaluation criteria are as follows:

[Evaluation Criteria]
◯: no changes
Δ: external aqueous medium being clouded and particles being slightly deformed
x: external aqueous medium being turbid and particles being deformed

TABLE 1

| Constituent of Cosmetic Composition (parts by weight) | Ex. I-1 | Ex. I-2 | Ex. I-3 | Comp. Ex. I-1 | Comp. Ex. I-2 | Comp. Ex. I-3 | Comp. Ex. I-4 | Comp. Ex. I-5 | Comp. Ex. I-6 |
|---|---|---|---|---|---|---|---|---|---|
| Carboxyvinyl polymer | 0.20 | — | — | 0.20 | — | — | 0.20 | — | — |
| Xanthane gum | — | 0.20 | — | — | 0.20 | — | — | 0.20 | — |
| Copolymer A | — | — | 0.20 | — | — | 0.20 | — | — | 0.20 |
| Potassium hydroxide | 0.10 | — | — | 0.10 | — | — | 0.10 | — | — |
| Succinic acid | — | — | 0.04 | — | — | 0.04 | — | — | 0.04 |
| Disodium hydrogenphosphate | — | — | 0.10 | — | — | 0.10 | — | — | 0.10 |
| Methyl paraoxybenzoate | 0.20 | 0.20 | 0.20 | 0.20 | 0.20 | 0.20 | 0.20 | 0.20 | 0.20 |
| Perfume | 0.10 | 0.10 | 0.10 | 0.10 | 0.10 | 0.10 | 0.10 | 0.10 | 0.10 |
| Purified water | Bal. | Bal. | Bal. | Bal. | Bal. | Bal. | Bal. | Bal. | Bal. |
| Hydrogel Particle 1 | 10.00 | 10.00 | 10.00 | — | — | — | — | — | — |
| Hydrogel Particle 2 | — | — | — | 10.00 | 10.00 | 10.00 | — | — | — |
| Physical Properties | | | | | | | | | |
| Moisturizing Effect | ◯ | ◯ | ◯ | ◯ | ◯ | ◯ | X | X | X |
| Smoothness on Skin | ◯ | ◯ | ◯ | Δ | Δ | Δ | ◯ | ◯ | ◯ |
| Residue of Particles on Skin | ◯ | ◯ | ◯ | X | X | X | — | — | — |
| Sphericity | ◯ | ◯ | ◯ | X | X | X | — | — | — |
| Storage Stability | | | | | | | | | |
| at 5° C. | ◯ | ◯ | ◯ | ◯ | ◯ | ◯ | — | — | — |
| at room temperature | ◯ | ◯ | ◯ | Δ | ◯ | ◯ | — | — | — |
| at 50° C. | ◯ | ◯ | ◯ | X | ◯ | ◯ | — | — | — |

(Note)
Copolymer A: N,N-dimethylaminoethyl methacrylate diethylsulfate/N,N-dimethylacrylamide/polyethylene glycol dimethacrylic acid terpolymer (molar ratio: 30/70/0.04)

It can be seen from the results shown in Table 1 that the cosmetic compositions obtained in Examples I-1 to I-3 are excellent in moisturizing effect and smoothness on skin, have no residue of particles on skin, and are excellent in storage stability since the hydrogel particles 1 are used.

Examples II-1 to II-10

The oil components were dissolved with heating at 80° C. in a compositional ratio shown in Table 2, to give an oil component solution. In addition, the aqueous components were dissolved with heating at 90° C. in a compositional ratio shown in Table 2, and cooled to 80° C. Thereafter, the oil component solution was added to the aqueous components, and the mixture was stirred with an anchor-type stirrer, to give a liquid mixture. The total amount of the oil components and the aqueous components before dissolving with heating was 500 g. Further, this liquid mixture was dispersed with an emulsifier commercially available from TOKUSHU KIKA KOGYO Co., Ltd. under the trade name of T.K. HOMO MIXER MARK, Model II 2.5 at 8000 r/min for one minute, to give a dispersion. This dispersion was discharged with heating at 80° C. into an oil [methyl polysiloxane: commercially available from Shin-Etsu Chemical Co., Ltd. under the trade name of KF-96A (20 CS)] cooled to 10° C. from an orifice having an orifice diameter of 1.2 mm at a flow rate of 10 mL/min. After the oil dispersion was allowed to separate into solid and liquid phases, the oil on the particle surface was removed, to give hydrogel particles.

Examples I-11 and II-12

The total amount of 500 g of the oil components and the aqueous components having a compositional ratio shown in Table 3 were dissolved with each other with heating in the same manner as in Example II-1, and the resulting mixture was discharged from the orifice in the same manner as in Example II-1, without dispersing the liquid mixture with an emulsifier, to give hydrogel particles.

Comparative Examples II-1 and II-2

The total amount of 500 g of the oil components and the aqueous components having a compositional ratio shown in Table 3 were dissolved with each other with heating in the same manner as in Example II-1, and the mixture was stirred with an anchor-type stirrer, to give a liquid mixture. Further, this liquid mixture was dispersed with an emulsifier commercially available from TOKUSHU KIKA KOGYO Co., Ltd. under the trade name of T.K. HOMO MIXER MARK II 2.5 at 8000 r/min for one minute, to give a dispersion. This dispersion was discharged into a 1% by weight aqueous calcium chloride solution at 20° C. from an orifice having an orifice diameter of 1.2 mm at a flow rate of 10 mL/min. After the oil dispersion was allowed to separate into solid and liquid phases, the 1% by weight aqueous calcium chloride solution on the particle surface was removed, to give hydrogel particles.

Comparative Examples II-3 and II-4

The total amount of 500 g of the oil components and the aqueous components having a compositional ratio shown in Table 3 were dissolved with each other with heating. As a result, the dispersion was gelated, thereby making it impossible to form particles.

Comparative Examples II-5 and II-6

The total amount of 500 g of the oil components and the aqueous components having a compositional ratio shown in Table 3 were dissolved with each other with heating, and the resulting mixture was discharged in the same manner as in Comparative Example II-1. As a result, the droplets were not gelated, thereby making it impossible to form particles.

TABLE 2

| Liquid Oil | Solid Fat | | Ex. II-1 | Ex. II-2 | Ex. II-3 | Ex. II-4 | Ex. II-5 | Ex. II-6 |
|---|---|---|---|---|---|---|---|---|
| | | Composition of Hydrogel Particle (% by weight) Dispersed Phase (Oil Phase) | | | | | | |
| ○ | | Fatty acid ester of dipentaerythritol | 15.0 | 15.0 | 25.0 | 15.0 | 2.5 | 2.5 |
| ○ | | Polyglyceryl diisostearate | 5.0 | 5.0 | — | 5.0 | 5.0 | 5.0 |
| ○ | | Methyl polysiloxane [commercially available from Shin-Etsu Chemical Co., Ltd. under the trade name of KF-96A (10 CS)] | 5.0 | 5.0 | 25.0 | 5.0 | 5.0 | 5.0 |
| | ○ | N-(2-Hydroxy-3-hexadecyloxypropyl)-N-2-hydroxyethylhexadecanamide (commercially available from Kao Corporation under the trade name of Sphingolipid E) | — | — | — | 10.0 | 10.0 | 10.0 |
| | ○ | Stearyl alcohol (commercially available from Kao Corporation under the trade name of KALCOL 80) | — | — | — | — | — | — |
| | ○ | Solid paraffin (commercially available from Nikko Rika K.K. under the trade name of CERESIN #810A) | — | — | — | — | — | — |
| — | | Sorbitan monostearate (commercially available from Kao Corporation under the trade name of RHEODOL SUPER SP-S10) | — | — | — | — | — | — |

| Liquid Oil | Solid Fat | | Ex. II-7 | Ex. II-8 | Ex. II-9 | Ex. II-10 | Ex. II-11 | Ex. II-12 |
|---|---|---|---|---|---|---|---|---|
| | | Composition of Hydrogel Particle (% by weight) Dispersed Phase (Oil Phase) | | | | | | |
| ○ | | Fatty acid ester of dipentaerythritol | 15.0 | 25.0 | 2.5 | 2.5 | 5.0 | 5.0 |
| ○ | | Polyglyceryl diisostearate | 5.0 | — | 5.0 | 5.0 | 10.0 | 10.0 |
| ○ | | Methyl polysiloxane [commercially available from Shin-Etsu Chemical Co., Ltd. under the trade name of KF-96A (10 CS)] | 5.0 | 17.5 | 5.0 | 5.0 | 5.0 | 5.0 |
| | ○ | N-(2-Hydroxy-3-hexadecyloxypropyl)-N-2-hydroxyethylhexadecanamide (commercially available from Kao Corporation under the trade name of Sphingolipid E) | 7.5 | 7.5 | — | — | 7.5 | 7.5 |
| | ○ | Stearyl alcohol (commercially available from Kao Corporation under the trade name of KALCOL 80) | — | — | 10.0 | — | — | — |

TABLE 2-continued

|  |  | Ex. No. | | | | | |
|---|---|---|---|---|---|---|---|
| ○ | Solid paraffin (commercially available from Nikko Rika K.K. under the trade name of CERESIN #810A) | — | — | — | 10.0 | — | — |
| — | Sorbitan monostearate (commercially available from Kao Corporation under the trade name of RHEODOL SUPER SP-S10) | — | — | — | 1.0 | 1.0 | |

|  | Ex. No. | | | | | |
|---|---|---|---|---|---|---|
|  | Ex. II-1 | Ex. II-2 | Ex. II-3 | Ex. II-4 | Ex. II-5 | Ex. II-6 |
| Composition of Hydrogel Particle (% by weight) | | | | | | |
| Continuous Phase (Aqueous Phase) | | | | | | |
| Deionized Water | Balance | Balance | Balance | 63.4 | 76.11 | 75.94 |
| Agar UP-16 (Gel Strength: 58.8 kPa) | — | 1.0 | 1.5 | 1.0 | 1.0 | 1.0 |
| Agar T-1 (Gel Strength: 88.2 kPa) | 0.5 | — | — | — | — | — |
| Methyl paraoxybenzoate | 0.3 | 0.3 | 0.3 | 0.3 | 0.3 | 0.3 |
| 86% Glycerol | — | — | — | — | — | — |
| Calcium lactate | — | — | — | — | — | — |
| Sodium polyoxyethylene lauryl ether phosphate (commercially available from Kao Corporation under the trade name of SPE104NB) | 0.3 | 0.05 | 0.1 | 0.3 | — | 0.05 |
| Copolymer of acrylic acid and alkyl methacrylate [commercially available from B. F. Goodrich under the trade name of PEMULEN (TR-1)] | — | 0.03 | 0.02 | — | 0.01 | 0.03 |
| 20% Aqueous polyoxyethylene octyl decyl ether (commercially available from Kao Corporation under the trade name of EMULGEN 2025G) | — | — | — | — | — | — |
| 1 N Aqueous sodium hydroxide | — | 0.18 | 0.11 | — | 0.08 | 0.18 |
| Viscosity of Dispersion at Discharging (mPa · s) | 40 | 45 | 300 | 55 | 50 | 35 |

|  | Ex. No. | | | | | |
|---|---|---|---|---|---|---|
|  | Ex. II-7 | Ex. II-8 | Ex. II-9 | Ex. II-10 | Ex. II-11 | Ex. II-12 |
| Composition of Hydrogel Particle (% by weight) | | | | | | |
| Continuous Phase (Aqueous Phase) | | | | | | |
| Deionized Water | 63.7 | 48.47 | Balance | Balance | 49.2 | Balance |
| Agar UP-16 (Gel Strength: 58.8 kPa) | 1.0 | 1.0 | 1.0 | 1.5 | 1.0 | 0.5 |
| Agar T-1 (Gel Strength: 88.2 kPa) | — | — | — | — | — | — |
| Methyl paraoxybenzoate | 0.3 | 0.3 | 0.3 | 0.3 | 0.3 | 0.3 |
| 86% Glycerol | — | — | — | — | 20.0 | 20.0 |
| Calcium lactate | 0.5 | — | — | — | — | — |
| Sodium polyoxyethylene lauryl ether phosphate (commercially available from Kao Corporation under the trade name of SPE104NB) | 1.0 | 0.1 | — | 0.05 | 1.0 | 1.0 |
| Copolymer of acrylic acid and alkyl methacrylate [commercially available from B. F. Goodrich under the trade name of PEMULEN (TR-1)] | — | 0.02 | 0.01 | 0.03 | — | — |
| 20% Aqueous polyoxyethylene octyl decyl ether (commercially available from Kao Corporation under the trade name of EMULGEN 2025G) | 1.0 | — | — | — | — | — |
| 1 N Aqueous sodium hydroxide | — | 0.11 | 0.08 | 0.18 | — | — |
| Viscosity of Dispersion at Discharging (mPa · s) | 70 | 255 | 60 | 40 | 120 | 100 |

TABLE 3

|  | Comp. Ex. No. | | | | | |
|---|---|---|---|---|---|---|
|  | Comp. Ex. II-1 | Comp. Ex. II-2 | Comp. Ex. II-3 | Comp. Ex. II-4 | Comp. Ex. II-5 | Comp. Ex. II-6 |
| Composition of Hydrogel Particle (% by weight) | | | | | | |
| Dispersed Phase (Oil Phase) | | | | | | |
| Fatty acid ester of dipentaerythritol | 2.5 | 15.0 | 15.0 | 15.0 | 25.0 | 25.0 |
| Polyglyceryl diisostearate | 5.0 | 5.0 | 5.0 | 5.0 | — | — |
| Methyl polysiloxane [commercially available from Shin-Etsu Chemical Co., Ltd. under the trade name of KF-96A (10 CS)] | 5.0 | 5.0 | 5.0 | 5.0 | 25.0 | 25.0 |

TABLE 3-continued

| | Comp. Ex. II-1 | Comp. Ex. II-2 | Comp. Ex. II-3 | Comp. Ex. II-4 | Comp. Ex. II-5 | Comp. Ex. II-6 |
|---|---|---|---|---|---|---|
| N-(2-Hydroxy-3-hexadecyloxypropyl)-N-2-hydroxyethylhexadecanamide (commercially available from Kao Corporation under the trade name of Sphingolipid E) | 10.0 | — | 5.0 | 7.5 | — | — |
| Sorbitan monostearate | | | | | | |
| Composition of Hydrogel Particle (% by weight) Continuous Phase (Aqueous Phase) | | | | | | |
| Deionized Water | 75.94 | Balance | 66.2 | Balance | 48.58 | Balance |
| Sodium alginate | 1.0 | 1.0 | 1.0 | 1.0 | 1.0 | 1.5 |
| Methyl paraoxybenzoate | 0.3 | 0.3 | 0.3 | 0.3 | 0.3 | 0.3 |
| 86% Glycerol | — | — | — | — | — | — |
| Calcium lactate | — | — | 0.5 | 0.5 | — | — |
| Sodium polyoxyethylene lauryl ether phosphate (commercially available from Kao Corporation under the trade name of SPE104NB) | 0.05 | 0.05 | 1.0 | 1.0 | 0.1 | 0.1 |
| Copolymer of acrylic acid and alkyl methacrylate [commercially available from B. F. Goodrich under the trade name of PEMULEN (TR-1)] | 0.03 | 0.03 | — | — | 0.02 | 0.02 |
| 20% Aqueous polyoxyethylene octyl decyl ether (commercially available from Kao Corporation under the trade name of EMULGEN 2025G) | — | — | 1.0 | 1.0 | — | — |
| 1 N Aqueous sodium hydroxide | 0.18 | 0.18 | — | — | — | — |
| Viscosity of Dispersion at Discharging (mPa · s) | 45 | 50 | — | Gelated | — | 500 |

Experiment

The properties of the dispersion before the formation of particles and the hydrogel particles obtained in each example and each comparative example were evaluated by the following methods. The results are shown in Table 4.

(1) Average Particle Diameter of Oil Component

With 50 g of water at 60° C. was diluted 0.5 g of the dispersion before the formation of particles. The average particle diameter of the oil component was determined using the diluted solution with a laser diffraction/scattering type particle size analyzer commercially available from Horiba, LTD. under the model number of LA-910.

(2) Average Particle Diameter of Hydrogel Particles 100 g of the particles were subjected to wet classification in water by using sieves with various mesh screens (opening of standard sieves prescribed in JIS Z 8801: 1000 to 4000 µm), and excess water was removed therefrom with filter paper. Thereafter, the weight-average particle diameter was determined by measuring the weight of the particles existing on each screen and calculating by using the average sieve size of the adjoining sieves.

(3) Breaking Intensity and Young's Modulus

The breaking intensity and Young's modulus were obtained from the breaking strength of the hydrogel particles and the slope of the load curve before break as determined by using a compression tester commercially available from NIDEC-SHIMPO Corporation under the trade name of FGX-0.2R; minimum determination load: 2 mN. As the measurement element, an adaptor having a planar shape was used, and the lowering speed of the measurement element was 10 mm/min and the temperature during the measurement was 25° C.

The breaking intensity and the Young's modulus of the hydrogel particles were obtained by using the cross-sectional area of the particles before measurement.

(4) Smoothness on Skin

The smoothness was determined in the same manner as above.

(5) Residue of Particles on Skin

The residue of particles on skin was determined in the same manner as above.

(6) Tackiness

Twenty panel testers conducted sensory evaluation for texture when the hydrogel particles were applied to skin. Its evaluation criteria are as follows:

[Evaluation Criteria]
5: not tacky
4: not much tacky
3: slightly tacky
2: somewhat tacky
1: markedly tacky Next, an average score of the test scores was obtained. When the average score is not less than 4, the texture was evaluated as "◯;" when the average score is not less than 2.5 and less than 4, the texture was evaluated as "Δ;" and when the average score is less than 2.5, the texture was evaluated as "x."

(7) Oil Leakage

A tightly closed vessel was charged with 100 parts by weight of the hydrogel particles and 75 parts by weight of a 20% by weight aqueous ethanol solution, and the mixture was stored at 40° C. for 24 hours. The oil component floating in the tightly closed vessel was visually observed, and a degree of difficulty in leakage of the oil component was evaluated as oil leakage on the basis of the following evaluation criteria.

[Evaluation Criteria]
◯: no oil float
Δ: slight oil float
x: obvious oil float (8) Sphericity A 3 g sample of the hydrogel particles was weighed, and the particles were dispersed in water over a petri dish so that the particles were not overlaid and photographed with a camera. A particle having a ratio of the longest diameter to the shortest diameter of not more than 1.7 was considered as a particle having a high sphericity. The longest diameter and the shortest diameter were determined for about 50 photographed particles. When not less than 80% by weight of the particles have a high sphericity, it was evaluated as "◯;" when less than 80% by weight and not less than 50% of the particles have a high sphericity, it was evaluated as "Δ;" and when less than 50% by weight of the particles have a high sphericity, it was evaluated as "x."

(9) Melting Point of Oil Component

The peak temperature of a DSC curve as determined by a differential scanning calorimeter commercially available from Perkin-Elmer under the trade name of DSC 7 differential scanning calorimeter at a heating rate of 2° C./min with a sample amount of 10 to 20 mg was defined as a melting point. The melting point for the oil component was determined for the oil component solution prepared in the same manner as in Examples II-1 to II-10.

nents, and the mixture was stirred with an anchor-type stirrer at 80° C., to give a liquid mixture. The total amount of the oil components and the aqueous components were 500 g. Further, this liquid mixture was dispersed with an emulsifier commercially available from TOKUSHU KIKA KOGYO Co., Ltd. under the trade name of T.K. HOMO MER MARK, Model II 2.5 at 8000 r/min for one minute, to give a dispersion. The dispersion was discharged with heating at 80° C. into an oil [methyl polysiloxane: commercially available from Shin-Etsu Chemical Co., Ltd. under the trade name of KF-96A (20 CS)] cooled to 10° C. from an orifice having an orifice diameter of 1.2 mm at a flow rate of 15 mL/min. During the preparation, the droplets were formed by vibrating the dispersion at a frequency of 60 Hz, and cooled to solidify. Thereafter, the particles were allowed to separate into solid

TABLE 4

| | Oil component | | Physical Properties of Hydrogel Particles | | | | | | | |
|---|---|---|---|---|---|---|---|---|---|---|
| No. | Average Particle Diameter [μm] | Melting Point [° C.] | Average Particle Diameter [μm] | Breaking Intensity [kPa] | Young's Modulus [kPa] | Smoothness on Skin | Residue of Particles on Skin | Tackiness | Oil Leakage | Sphericity |
| Ex. II-1 | 4 | less than 35 | 3200 | 14 | 118 | ◯ | ◯ | Δ | Δ | ◯ |
| Ex. II-2 | 6 | less than 35 | 3200 | 13 | 119 | ◯ | ◯ | ◯ | Δ | ◯ |
| Ex. II-3 | 12 | less than 35 | 3100 | 35 | 145 | ◯ | ◯ | ◯ | Δ | ◯ |
| Ex. II-4 | 5 | 69 | 3200 | 15 | 125 | ◯ | ◯ | Δ | ◯ | ◯ |
| Ex. II-5 | 25 | 69 | 3100 | 7 | 43 | ◯ | ◯ | ◯ | ◯ | ◯ |
| Ex. II-6 | 8 | 69 | 3200 | 12 | 60 | ◯ | ◯ | ◯ | ◯ | ◯ |
| Ex. II-7 | 7 | 67 | 3000 | 28 | 95 | ◯ | ◯ | Δ | ◯ | ◯ |
| Ex. II-8 | 10 | 67 | 3100 | 20 | 80 | ◯ | ◯ | ◯ | ◯ | ◯ |
| Ex. II-9 | 26 | 58 | 3100 | 8 | 45 | ◯ | ◯ | ◯ | ◯ | ◯ |
| Ex. II-10 | 14 | 66 | 3200 | 30 | 95 | ◯ | ◯ | ◯ | ◯ | ◯ |
| Ex. II-11 | 25 | 67 | 3100 | 21 | 110 | ◯ | ◯ | Δ | ◯ | ◯ |
| Ex. II-12 | 25 | 67 | 3100 | 5 | 70 | ◯ | ◯ | Δ | ◯ | ◯ |
| Comp. Ex. II-1 | 8 | 69 | 3100 | 43 | 155 | Δ | Δ | ◯ | Δ | Δ |
| Comp. Ex. II-2 | 7 | less than 35 | 3000 | 39 | 173 | Δ | Δ | Δ | X | Δ |
| Comp. Ex. II-3 | The dispersion was gelated before the formation of particles, thereby making it impossible to form particles. | | | | | | | | | |
| Comp. Ex. II-4 | The dispersion was gelated before the formation of particles, thereby making it impossible to form particles. | | | | | | | | | |
| Comp. Ex. II-5 | The droplets were not gelated, thereby making it impossible to form particles. | | | | | | | | | |
| Comp. Ex. II-6 | 12 | The droplets were not gelated, thereby making it impossible to form particles. | | | | | | | | |

It can be seen from the comparison of Example II-2 with Comparative Example II-2 that when a non-crosslinked hydrogel is used in the hydrogel particles, the hydrogel is excellent in smoothness and free from residue of particles and tackiness, so that the particles having improved oil leakage can be obtained. In addition, it can be seen from the comparison of Example II-7 with Comparative Examples II-3 and II-4 that there is no compositional limitation in Example II-7. Further, it can be seen from the comparison of Examples II-3 and II-8 with Comparative Examples II-5 and II-6 that the particles can be formed even when the content of the oil component is high.

Examples III-1 and III-2

The oil components having a compositional ratio shown in Table 5 were dissolved with heating at 80° C., and the aqueous components having a compositional ratio shown in Table 5 were dissolved with heating at 90° C., and cooled to 80° C. The oil components were mixed with the aqueous compoand liquid phases and washed, to give hydrogel particles having high monodispersibility. The viscosity of the dispersion at discharging was 55 mPa·s (55 cP).

Examples III-3 and III-4

The oil components having a compositional ratio shown in Table 5 were dissolved with heating at 80° C., and the aqueous components having a compositional ratio shown in Table 5 were dissolved with heating at 90° C., and cooled to 80° C. The oil components were mixed with the aqueous components, and the mixture was stirred with an anchor-type stirrer at 80° C., and talc was further added thereto, to give a liquid mixture. The total amount of the oil component, the aqueous component and talc was 500 g. The liquid mixture was treated in the same manner as in Example III-1, to give hydrogel particles having high monodispersibility. The viscosity of the dispersion at discharging was 65 mPa·s (65 cP).

TABLE 5

| | Ex. No. | | | |
|---|---|---|---|---|
| | Ex. III-1 | Ex. III-2 | Ex. III-3 | Ex. III-4 |
| Composition of Hydrogel Particle (% by weight) | | | | |
| Oil Phase | | | | |
| Fatty acid ester of dipentaerythritol | 15.0 | 5.0 | 15.0 | 5.0 |
| Polyglyceryl diisostearate | 5.0 | 10.0 | 5.0 | 10.0 |
| Methyl polysiloxane [commercially available from Shin-Etsu Chemical Co., Ltd. under the trade name of KF-96A] | 5.0 | 5.0 | 5.0 | 5.0 |
| N-(2-Hydroxy-3-hexadecyloxypropyl)-N-2-hydroxyethylhexadecanamide (commercially available from Kao Corporation under the trade name of Sphingolipid E) | 10.0 | 10.0 | 10.0 | 10.0 |
| Aqueous Phase | | | | |
| Deionized Water | 63.4 | 69.14 | 62.4 | 68.14 |
| Agar UP-16 (commercially available from Ina Shokuhin Kogyo K.K.) | 1.0 | 0.5 | 1.0 | 0.5 |
| Methyl paraoxybenzoate | 0.3 | 0.3 | 0.3 | 0.3 |
| Sodium polyoxyethylene lauryl ether phosphate (commercially available from Kao Corporation under the trade name of SPE-104NB) | 0.3 | 0.05 | 0.3 | 0.05 |
| Copolymer of acrylic acid and alkyl methacrylate [commercially available from B. F. Goodrich under the trade name of PEMULEN (TR-1)] | — | 0.01 | — | 0.01 |
| Talc (powder) [commercially available from K.K. Yamaguchi Ummo Kogyosho] | — | — | 1.0 | 1.0 |

Evaluation

Next, the following evaluation was made by using the hydrogel particles obtained in each of Examples and Comparative Examples. The results are shown in Table 6.

(1) Average Particle Diameter of Hydrogel Particles

The average particle diameter was determined in the same manner as above.

(2) Sphericity

The sphericity was determined in the same manner as above.

(3) Monodispersibility

The monodispersibility was evaluated by obtaining a CV value from a standard deviation and arithmetic means of the determined particle diameter. The longest diameter of the particle obtained when determining the sphericity was defined as the particle diameter of the particle. Those having a CV value of not more than 5 are evaluated as excellent monodispersibility. The longest particle diameter and the shortest particle diameter are also shown in Table 6. The smaller the difference therebetween is, the more excellent the monodispersibility is.

TABLE 6

| | Physical Properties of Hydrogel Particles | | | | | |
|---|---|---|---|---|---|---|
| | | | Monodispersibility | | | |
| Ex. No. | Average Particle Diameter [μm] | Sphericity | Shortest Particle Diameter [mm] | Longest Particle Diameter [mm] | CV Value | Evaluation |
| III-1 | 2.04 | ○ | 1.95 | 2.10 | 1.30 | Excellent |
| III-2 | 2.01 | ○ | 1.93 | 2.10 | 1.28 | Excellent |
| III-3 | 1.98 | ○ | 1.91 | 2.08 | 1.25 | Excellent |
| III-4 | 2.00 | ○ | 1.90 | 2.07 | 1.29 | Excellent |

It can be seen from the results shown in Table 6 that the hydrogel particles obtained in each example have high sphericity and are excellent in monodispersibility.

The skin cosmetic composition of the present invention shows excellent appearance because particles are dispersed and suspended in a liquid medium. Also, the skin cosmetic composition is excellent in storage stability and smoothness, and no residue of particles remains on skin when the skin cosmetic composition is applied to the skin. Therefore, the skin cosmetic composition favorably exhibits the effects based on the ingredients. In the skin cosmetic composition of the present invention, the particles are easily broken when applied to skin, so that the ingredients are uniformly smoothened over the skin, thereby realizing a refreshing feel without being tacky.

When the hydrogel particles of the present invention are applied to skin and rubbed with fingers, the particles are smoothly broken, so that there are exhibited such effects that the hydrogel particles are easily smoothened, have no residue of particles and excellent breaking ability. In addition, the hydrogel particles of the present invention exhibit some effects such that there is no leakage of the oil component from the particles, without giving tackiness during application.

What is claimed is:

1. A process for preparing hydrogel particles comprising:
discharging an O/W dispersion, which is prepared by dissolving a water-soluble polymer capable of forming a non-crosslinked hydrogel in an aqueous solution and emulsifying an oil component therein, with vibration at a frequency of 5 to 200 Hz from an orifice to form droplets; and
cooling the droplets to solidify
wherein said oil component comprises a solid fat and a liquid oil; and
wherein an average particle diameter of said oil component is not more than 10% of the particle diameter of said hydrogel.

2. The process according to claim 1, wherein the oil component is emulsified or dispersed in the aqueous component solution with at least one of an emulsifying agent and a dispersing agent.

3. The process according to claim 1, wherein the non-crosslinked hydrogel comprises at least one of agar or gelatin.

4. The process according to claim 1, wherein the non-crosslinked hydrogel comprises agar having a gel strength of not more than 68.6 kPa.

5. The process according to claim 1, wherein not less than 80% by weight of the hydrogel particles have a ratio of a longest diameter to a shortest diameter (longest diameter/a shortest diameter) of not more than 1.7.

6. The process according to claim 1, wherein the hydrogel particles have a CV value for particle diameter of 5 or less.

7. The process according to claim 1, wherein the hydrogel particles have a shape having rotation symmetry.

8. The process according to claim 1, wherein the hydrogel particles are spherical.

9. The process according to claim 1, wherein the orifice has a diameter of from 0.1 to 5 mm.

10. The process according to claim 1, wherein said droplets are cooled in the atmosphere.

11. The process according to claim 1, wherein said droplets are cooled in a liquid.

12. The process according to claim 11, wherein said liquid is selected from the group consisting of a liquid stream having a downward flow, a liquid steam having an upward flow or a liquid stream having a concurrent flow.

13. The process according to claim 1, wherein said O/W dispersion is discharged at a temperature which is not less than a gelation temperature of said dispersion.

14. The process according to claim 1, wherein said droplets are cooled at a temperature which is not more than a gelation temperature of said dispersion.

15. The process according to claim 1, wherein said droplets are cooled at a temperature not more than 40° C.

16. The process according to claim 1, wherein said droplets are cooled at a temperature not more than 20° C.

17. The process according to claim 1, wherein a continuous phase of said O/W dispersion comprises 40-99 wt. % of said dispersion.

18. The process according to claim 1, wherein said non-crosslinked hydrogel comprises 0.25 to 5.1 wt. % of said water-soluble polymer in a continuous phase.

19. The process according to claim 1, wherein an oil component of said O/W dispersion comprises 1 to 80 wt. % of a solid fat and 20 to 99 wt. % of a liquid oil.

20. The process according to claim 1, wherein an oil component of said O/W dispersion comprise 0.001 to 20 wt. % of an emulsifying agent.

* * * * *